United States Patent
Cooper

(10) Patent No.: US 10,345,237 B1
(45) Date of Patent: Jul. 9, 2019

(54) SPECTRAL EDGE DETECTION

(71) Applicant: RareCyte, Inc., Seattle, WA (US)

(72) Inventor: Jeremy Ryan Cooper, North Bend, WA (US)

(73) Assignee: RareCyte, Inc., Seattle, WA (US)

( * ) Notice: Subject to any disclaimer, the term of this patent is extended or adjusted under 35 U.S.C. 154(b) by 0 days.

(21) Appl. No.: 16/264,490

(22) Filed: Jan. 31, 2019

(51) Int. Cl.
| | |
|---|---|
| G01N 21/43 | (2006.01) |
| G01N 21/78 | (2006.01) |
| G01N 21/64 | (2006.01) |

(52) U.S. Cl.
CPC ......... *G01N 21/6428* (2013.01); *G01N 21/78* (2013.01); *G01N 2021/6439* (2013.01); *G01N 2201/063* (2013.01)

(58) Field of Classification Search
CPC ... A61B 5/0059; A61B 5/7264; A61B 5/7257; A61B 5/7267; G01N 21/31
USPC ........................................................ 436/172
See application file for complete search history.

(56) References Cited

U.S. PATENT DOCUMENTS

| | | | |
|---|---|---|---|
| 3,390,604 A | 7/1968 | Makabe | |
| 3,861,788 A | 1/1975 | Webster | |
| 4,082,464 A | 4/1978 | Johnson, Jr. | |
| 4,084,909 A | 4/1978 | Mathisen | |
| 4,176,916 A | 12/1979 | Carpenter | |
| 5,081,689 A * | 1/1992 | Meyer | G06T 7/12 |
| | | | 382/199 |
| 5,214,494 A | 5/1993 | Inaba et al. | |
| 5,591,981 A | 1/1997 | Heffelfinger et al. | |
| 5,689,317 A | 11/1997 | Miller | |
| 5,710,663 A | 1/1998 | Kawasaki | |
| 5,852,498 A | 12/1998 | Youvan et al. | |
| 5,892,612 A | 4/1999 | Miller et al. | |
| 5,953,087 A | 9/1999 | Hoyt | |
| 6,262,837 B1 | 7/2001 | Nagano et al. | |
| 6,422,994 B1 | 7/2002 | Kaneko et al. | |
| 6,894,838 B2 | 5/2005 | Mizrahi et al. | |
| 7,321,791 B2 | 1/2008 | Levenson et al. | |
| 7,555,155 B2 | 6/2009 | Levenson et al. | |
| 7,655,898 B2 | 2/2010 | Miller | |
| 8,059,327 B1 | 11/2011 | Erdogan et al. | |
| 8,280,134 B2 | 10/2012 | Hoyt | |
| 8,634,607 B2 | 1/2014 | Levenson et al. | |
| 9,074,937 B2 | 7/2015 | Kuo et al. | |
| 9,304,237 B1 | 4/2016 | Wang et al. | |
| 9,547,178 B2 | 1/2017 | Erdogan et al. | |
| 9,607,374 B2 | 3/2017 | Azar et al. | |
| 9,624,540 B2 | 4/2017 | Lundquist et al. | |
| 9,654,745 B2 | 5/2017 | Zeng et al. | |
| 9,792,693 B2 | 10/2017 | Bamford et al. | |
| 9,996,924 B2 | 6/2018 | Chukka et al. | |
| 10,012,537 B2 | 7/2018 | Garsha et al. | |
| 10,150,988 B2 | 12/2018 | Diehl et al. | |
| 10,151,701 B2 | 12/2018 | Xu et al. | |
| 2006/0061761 A1 | 3/2006 | Li et al. | |
| 2011/0110567 A1 * | 5/2011 | Jiang | A61B 5/0059 |
| | | | 382/128 |
| 2019/0052792 A1 * | 2/2019 | Baba | H04N 5/2355 |

* cited by examiner

*Primary Examiner* — Rebecca M Fritchman
(74) *Attorney, Agent, or Firm* — Shay Glenn LLP

(57) ABSTRACT

This disclosure relates generally to detecting multiple biomarkers on or within a sample, though more specifically, to detecting individual detection moieties within a plurality of detection moieties.

26 Claims, 12 Drawing Sheets

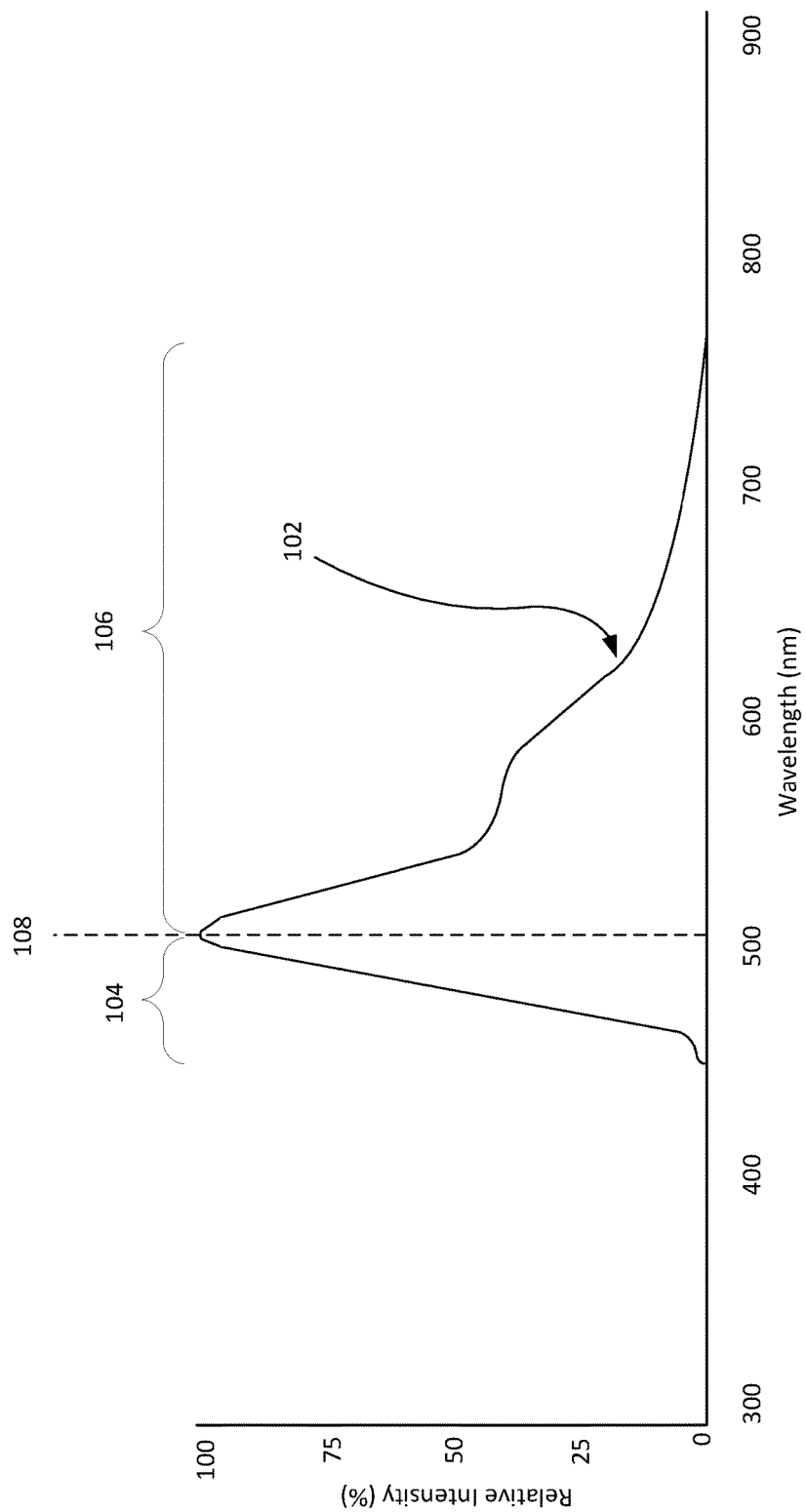

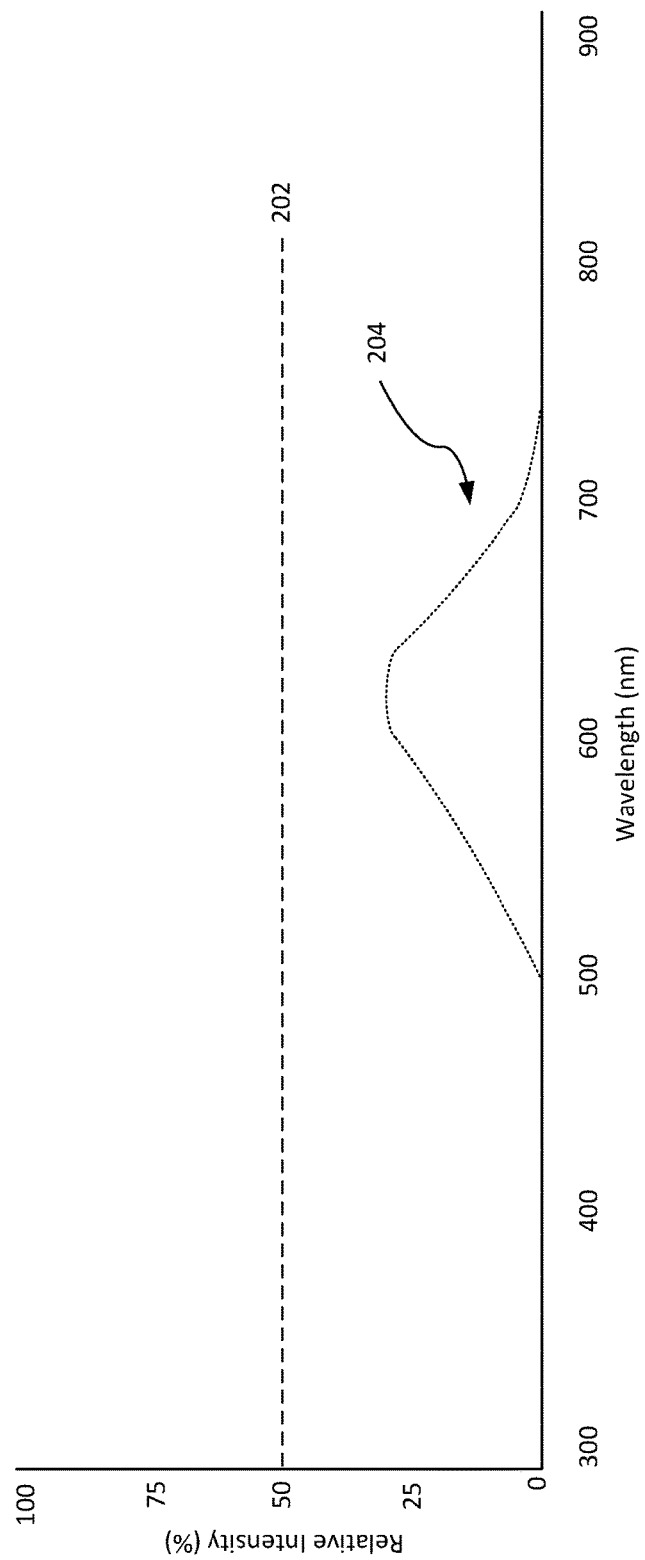

SPECTRAL EDGE DETECTION

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

This disclosure relates generally to detecting multiple biomarkers on or within a sample, though more specifically, to detecting individual detection moieties within a plurality of detection moieties.

BACKGROUND

Samples often include materials of interest that are to be imaged for analysis. These materials of interest may include a plurality of biomarkers and/or components for which it may be desirous to detect and image. Current filters and imaging apparatuses may only permit for a limited number of labels to be used at any one given time. As a result, practitioners, researchers, and those working with suspensions continue to seek systems and methods to more efficiently and accurately image samples.

BRIEF DESCRIPTION OF THE DRAWINGS

FIG. 1A shows an example first emission spectrum.
FIG. 2A shows an example fourth emission spectrum and a background signal.

DETAILED DESCRIPTION

Figure 1B:
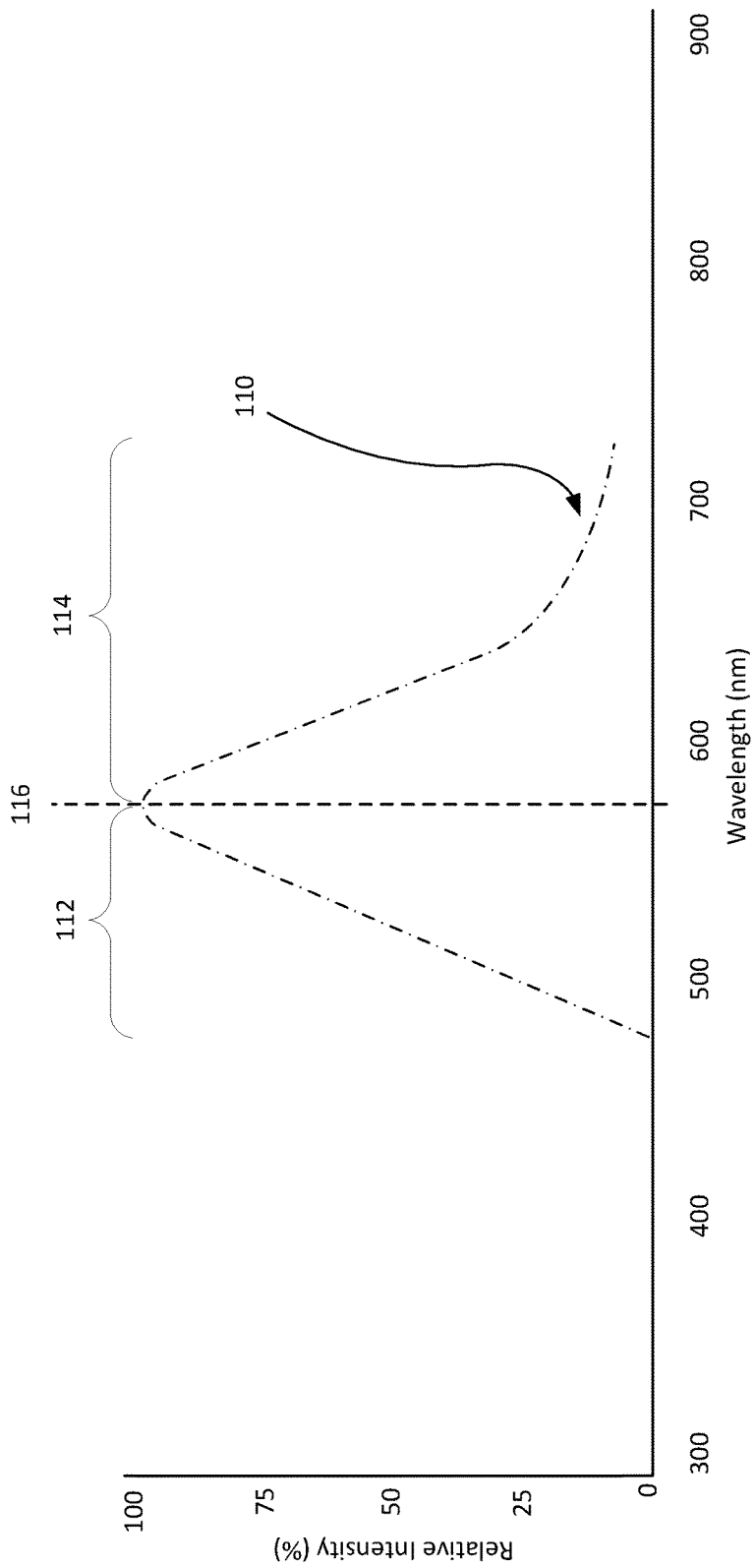
FIG. 1B shows an example second emission spectrum.

This disclosure is directed to a system and method for obtaining spectral data of individual detection moieties from a plurality of detection moieties, such as those detection moieties having overlapping spectra, based on emission and/or excitation wavelengths of the respective detection moieties used. This disclosure is further directed to a system and method for recording fluorescent images while distinguishing between multiple separate fluorescent targets.

In the following description, the term "raw image" is used to describe an image (whether or not visually displayed to an operator or end user) including data or at least one signal, having been captured by a sensor or detector, which has not been processed.

In the following description, the term "final image" is used to describe an image (whether or not visually displayed to an operator or end user) including data or at least one signal which has been processed. "Final image" can also be used to describe an image (whether or not visually displayed to an operator or end user) which is an output image resulting from the comparison and/or analysis of two or more raw or other final images.

In the following descriptions, the term "light" is used to describe various uses and aspects of multiplexing and imaging. The term light is not intended to be limited to describing electromagnetic radiation in the visible portion of the electromagnetic spectrum, but is also intended to describe radiation in the ultraviolet and infrared portions of the electromagnetic spectrum.

In the following descriptions, the term "sample" is used to describe a biological fluid, a biological semi-solid, a biological solid (which may remain solid, such as tissue, or may be liquefied in any appropriate manner), a suspension, a portion of the suspension, a component of the suspension, or the like.

In the following descriptions, the terms "target analyte" or "target material" are used to describe a biological material of interest.

In the following descriptions, the term "non-target analyte" is used to describe a biological material which is not a target analyte.

In the following descriptions, the term "biomarker" is used to describe a substance that is present on or within the target analyte or target material (i.e. intracellular or extracellular the target analyte; internalized, such as through phagocytosis, within the target analyte; or the like). Biomarkers include, but are not limited to, peptides, proteins, subunits, domains, motifs, epitopes, isoforms, DNA, RNA, or the like. The biomarker may be a target molecule for drug delivery.

In the following descriptions, the term "affinity molecule" is used to describe any molecule that is capable of binding to or interacting with another molecule. The interaction or binding can be covalent or non-covalent. The affinity molecule includes, but is not limited to, an antibody, a hapten, a protein, an aptamer, an oligonucleotide, a polynucleotide, or any appropriate molecule for interacting with or binding to another molecule (e.g., a biomarker; a molecule of a binding pair or a complementary molecule, including, without limitation, biotin or an avidin; or, the like).

In the following descriptions, the term "detection moiety" is used to describe a compound or substance which provides a signal for detection, thereby indicating the presence of another compound or substance, an analyte, or the like within a sample or specimen. The detection moiety can be fluorescent, such as a fluorescent probe, or chromogenic, such as a chromogenic dye. The fluorescent probe can be a reactive dye, an organic dye, a fluorescent protein, a quantum dot, non-protein organic molecules, a nanoparticle (e.g., nanodiamond), or the like.

The detection moiety is a compound or substance which provides a signal for detection, thereby indicating the presence of another compound or substance, an analyte, or the like within a sample or specimen. The detection moiety can be used as a tracer, as a label for certain structures, as a label for biomarkers, or the like. The detection moiety can be distributed or can label the appropriate structure or biomarkers in manners including, but not limited to, uptake, selective uptake, diffusion, and attachment to a linking molecule. The detection moiety can be bound to the biomarker by direct labeling or by indirect labeling.

The chromogenic dye, which can be used with various enzyme labels (e.g. horseradish peroxidase and alkaline phosphate), includes, but is not limited to, 3,3'-Diaminobenzidine (DAB), 3-Amino-9-Ethylcarbazole (AEC), 4-Chloro- 1-Naphtol (CN), P-Phenylenediamine Dihydrochloride/pyrocatechol (Hanker-Yates reagent), Fast Red TR, New Fuchsin, Fast Blue BB, or the like. Fluorescent probes include, but are not limited to 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AutoFluorescent Protein; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H; Blue Fluorescent Protein); BFP/GFP FRET; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Brilliant Violet 421; Brilliant Violet 510; Brilliant Violet 605; Brilliant Violet 650; Brilliant Violet 711; Brilliant Violet 786; BTC; BTC-5N; Calcein; Calcein Blue; Calcium Crimson™; Calcium Green; Calcium Green-1; Calcium Green-2; Calcium Green-5N; Calcium Green-C18; Calcium Orange; Calcofluor White; Carboxy-X-hodamine (5-ROX); Cascade Blue™; Cascade Yellow; Catecholamine; CCF2 (GeneBlazer); CFDA; CFP (Cyan Fluorescent Protein); CF405S; CF488A; CF 488; CF 543; CF 647; CF 750; CF 760; CF 780; FP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); CyQuant Cell Proliferation Assay; Dabcyl; Dansyl; Dansyl Amine; Dansyl Cadaverine; Dansyl Chloride; Dansyl DHPE; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS; DiA (4-Di-16-ASP); Dichlorodihydrofluorescein Diacetate (DCFH); DiD-Lipophilic Tracer; DiD (DiIC18(5)); DIDS; Dihydorhodamine 123 (DHR); DiI (DiIC18(3)); Dinitrophenol; DiO (DiOC18(3)); DiR; DiR (DiIC18(7)); DM-NERF (high pH); DNP; Dopamine; DsRed; DTAF; DY-630-NHS; DY-635-NHS; EBFP (Enhanced Blue Fluorescent Protein); ECFP (Enhanced Cyan Fluorescent Protein); EGFP (Enhanced Green Fluorescent Protein); ELF 97; Eosin; ER-Tracker™ Green; ER-Tracker™ Red; ER-Tracker™ Blue-White DPX; Erythrosin; Erythrosin ITC; Ethidium Bromide; Ethidium homodimer-1 (EthD-1); Euchrysin; EukoLight; Europium (III) chloride; EYFP (Enhanced Yellow Fluorescent Protein); Fast Blue; FDA; FIF (Formaldehyde Induced Fluorescence); FITC; FITC Antibody; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2, high calcium; Fura-2, low calcium; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green; Mitotracker Orange; Mitotracker Red; Mitramycin; Monobromobimane; Monobromobimane (mBBr-GSH); Monochlorobimane; MPS (Methyl Green Pyronine Stilbene); mStrawberry; NBD; NBD Amine; Nile Red; Nitrobenzoxadidole; Noradrenaline; Nuclear Fast Red; Nuclear Yellow; Nylosan Brilliant Iavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B; Phycoerythrin R; PKH26 (Sigma); PKH67; PMIA; Pontochrome Blue Black; POPO-1; POPO-3; PO-PRO-1; PO-PRO-3; Primuline; Procion Yellow; Propidium Iodid (PI); Pyrene; Pyronine; Pyronine B; Pyrozal Brilliant Flavin 7GF; QD400; QD425; QD450; QD500; QD520; QD525; QD530; QD535; QD540; QD545; QD560; QD565; QD570; QD580; QD585; QD590; QD600; QD605; QD610; QD620; QD625; QD630; QD650; QD655; QD705; QD800; QD1000; QSY 7; Quinacrine Mustard; Red 613 (PE-TexasRed); Resorufin; RFP; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin; rsGFP (red shifted GFP (S65T)); S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgGFP™ (super glow GFP; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; SYTOX Red; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TetramethylRodamineIsoThioCyanate; True Blue; TruRed; Tubulin Tracker™ Green; Ultralite; Uranine B; Uvitex SFC; wt GFP (wild type GFP); WW 781; X-Rhodamine; XRITC; Xylene Orange; Y66F; Y66H; Y66W; Yellow GFP (Yellow shifted); Green Fluorescent Protein; YFP (Yellow Fluorescent Protein); YO-PRO-1; YO-PRO-3; YOYO-1; YOYO-3; and, combinations and derivatives thereof. In one embodiment, the detection moiety, such as organic fluorophore, can have a molecule weight of at least 1 kD, including, without limitation, at least 10 kD, at least 25 kD, at least 50 kD, at least 75 kD, at least 100 kD, at least 150 kD, at least 200 kD, at least 250 kD, at least 300 kD, at least 340 kD, at least 350 kD, at least 500 kD, and at least 750 kD.

In the following descriptions, the terms "stain" or "label," which are used interchangeably, are used to describe an affinity molecule bound to or interacted with a detection moiety. The binding or interaction can be direct or indirect. Direct binding or interaction includes covalent or non-covalent interactions between the biomarker and the detection moiety. Indirect binding or interaction includes the use of at least first and second complementary molecules which form binding pairs. The first and second complementary molecules are, in combination, binding pairs which can bind or interact in at least one of the following manners: hydrophobic interactions, ionic interactions, hydrogen bonding interactions, non-covalent interactions, covalent interactions, affinity interactions, or the like. The binding pairs include, but are not limited to, immune-type binding-pairs, such as, antigen-antibody, antigen-antibody fragment, hapten-anti-hapten, or primary antibody-secondary antibody; nonimmune-type binding-pairs, such as biotin-avidin, biotin-streptavidin, folic acid-folate binding protein, hormone-hormone receptor, lectin-specific carbohydrate, enzyme-enzyme, enzyme-substrate, enzyme-substrate analog, enzyme-pseudo-substrate (substrate analogs that cannot be catalyzed by the enzymatic activity), enzyme-cofactor, enzyme-modulator, enzyme-inhibitor, or vitamin B12-intrinsic factor. Other suitable examples of binding pairs include complementary nucleic acid fragments (including complementary nucleotides, oligonucleotides, or polynucleotides); Protein A-antibody; Protein G-antibody; nucleic acid-nucleic acid binding protein; polymeric linkers (e.g., polyethylene glycol); or polynucleotide-polynucleotide binding protein. The binding pairs can be included within or used as amplification techniques. Amplification techniques are also implemented to increase the number of detection moieties bound to or interacted with the biomarker to increase a signal. In one embodiment, when binding pairs are used, the stain can be pre-conjugated, such that, during a labeling, staining, or adding step, the affinity molecule is already bound to or interacted with a detection moiety when added to the sample. In one embodiment, when binding pairs are used, the stain can be conjugated in the sample, such that the labeling, staining, or adding step includes at least two sub-steps including introducing (in any desired or appropriate order) an affinity molecule-first binding molecule conjugate and a second binding pair molecule-detection moiety conjugate, wherein the first and second binding pair molecules are complementary and bind to or interact with each other.

Furthermore, "a plurality of stains" can be used to describe two or more stains in which the affinity molecules and/or the detection moieties are different. For example, anti-CK-Alexa 647 is different than anti-EpCAM-Alexa 647. As another example, anti-CK-Alexa 647 is different than anti-CK-Alexa 488.

In the following descriptions, the term "conjugate" is used to describe a first chemical, molecule, moiety, or the like bound to or interacted with a second chemical, molecule, moiety, or the like. The binding or interaction is direct or indirect. Direct binding or interaction includes covalent or non-covalent interactions between the biomarker and the detection moiety. Indirect binding or interaction includes the use of at least first and second complementary molecules which form binding pairs. The first and second complementary molecules are, in combination, binding pairs which binds or interacts in at least one of the following manners: hydrophobic interactions, ionic interactions, hydrogen bonding interactions, non-covalent interactions, covalent interactions, affinity interactions, or the like. The binding pairs include, but are not limited to, immune-type binding-pairs, such as, antigen-antibody, antigen-antibody fragment, hapten-anti-hapten, or primary antibody-secondary antibody; nonimmune-type binding-pairs, such as biotin-avidin, biotin-streptavidin, folic acid-folate binding protein, hormone-hormone receptor, lectin-specific carbohydrate, enzyme-enzyme, enzyme-substrate, enzyme-substrate analog, enzyme-pseudo-substrate (substrate analogs that cannot be catalyzed by the enzymatic activity), enzyme-cofactor, enzyme-modulator, enzyme-inhibitor, or vitamin B12-intrinsic factor. Other suitable examples of binding pairs include complementary nucleic acid fragments (including complementary nucleotides, oligonucleotides, or polynucleotides); Protein A-antibody; Protein G-antibody; nucleic acid-nucleic acid binding protein; polymeric linkers (e.g., polyethylene glycol); or polynucleotide-polynucleotide binding protein.

In the following description, the term "signal" is used to describe an electric current or electromagnetic field which conveys data from one place or source to another place or detector. For example, a signal can be light emitted by a detection moiety to convey the presence of the detection moiety on or within a target analyte, such as a cell.

In the following description, the term "multiplex" is used to describe process or kit by which a sample is labeled with a plurality of stains. Each of the detection moieties emit different wavelengths. For example, at least two stains can be used to label the sample. Multiplexing can include up to 2, 4, 6, 8, 10, 12, 16, 20, 24, 30, 40, 50, 60, 70, 80, 90, 100, or more stains.

An example method for labeling a biomarker on a target analyte is discussed. In one embodiment, a sample, suspected of including at least one target analyte is obtained. Suitable devices, systems, and/or methods of sample collection and/or processing may include those described in one or more of the following U.S. patents and published applications, each of which is hereby incorporated by reference in its entirety: U.S. Pat. Nos. 7,074,577; 7,220,593; 7,329,534; 7,358,095; 7,629,176; 7,915,029; 7,919,049; 8,012,742; 9,039,999; 9,217,697; 9,492,819; 9,513,291; 9,533,303; 9,539,570; 9,541,481; 9,625,360; 2014/0161688; 2017/0014819; 2017/0059552; 2017/0074759. Suitable devices, systems, and/or methods for target analyte retrieval, isolation, or picking may include those described in one or more of the following U.S. patents and published applications, each of which is hereby incorporated by reference in its entirety: U.S. Pat. Nos. 9,222,953; 9,440,234; 9,519,002; 9,810,605; 2017/0219463; 2017/0276575.

In one embodiment, the sample can undergo staining after collection of the sample. In one embodiment, the sample can undergo staining after processing the sample. In one embodiment, the sample can be multiplexed. At least one stain is added to the sample for labeling, such as by an autostainer or manually by an operator. In one embodiment, the at least one target analyte is stained. In one embodiment, at least one non-target analyte or non-target material is stained. In one embodiment, the at least one target analyte and the at least one non-target analyte or materials are stained.

After staining, the sample can be imaged, whereby the stained sample is illuminated with one or more wavelengths of excitation light, such as infrared, red, blue, green, and/or ultraviolet, from a light source, such as a laser or a light-emitting diode. The imaging can be done with a flow cytometer or a microscope, such as a fluorescent microscope, a scanner, or any other appropriate imaging system or modality. In one embodiment, imaging can be performed in a system in which a detection moiety, when imaged, can provide a signal across a spectrum, including, without limitation, brightfield and/or darkfield illumination, fluorescence, and the like. The images formed can be overlaid when a plurality of detection moieties are used. Emission, reflection, diffraction, scatter, and combinations thereof are used in for detection/imaging. The images can be analyzed to detect, enumerate, and/or locate the target analyte, such as when it is desirous to retrieve or pick the target analyte. Imaging is performed in a tube, on a microscope slide, or in any appropriate vessel or substrate for imaging.

The methods can be performed by at least one of an imaging microscope, a scanner, a flow cytometer, or a microfluidic device, such as a chip or a microchannel, or the method can be performed by any combination of the above. The methods described can be used in a system in which a detection moiety, when imaged, can provide a signal across a spectrum, including, without limitation, brightfield and/or darkfield illumination, fluorescence, and the like.

Spectral Edge Detection

Spectral edge detection is a process by which individual detection moieties can be distinguished from a plurality of detection moieties (i.e., during multiplexing), such as by distinguishing the detection moieties orthogonally—in that there is no ambiguity as to which detection moiety is being detected and/or imaged. A feature of a signal of interest, such as from a detection moiety of interest, can be distinguished in the presence of a featureless signal (i.e., the signal has an unknown value and/or structure), such as from background, autofluorescence, or a non-desired detection moiety. In other words, spectral edge detection determines the contribution of a detection moiety of interest across a plurality of signals (or images) composed of contributions from a plurality of detection moieties having at least partially overlapping spectra by eliminating the contributions from the non-desired detection moieties across the plurality of the signals (or images) when the intensities (and therefore the respective contributions) of the detection moieties are unknown.

In one embodiment, spectral edge detection, unlike other detection systems which obtain detection moiety information at peak emission, uses an edge (e.g., a trailing edge or a leading edge) of an emission or excitation spectrum, such as for a detection moiety, to identify a single detection moiety. In one embodiment, spectral edge detection obtains data points to form a curve for a first detection moiety and data points to form a line for a second detection moiety, such that at least a portion of the line falls under the curve.

FIG. 1A shows an emission spectrum 102 of a first detection moiety. The emission spectrum 102 includes a leading spectral edge 104 and a trailing spectral edge 106. In other words, the leading spectral edge 104 is a portion of the emission spectrum 102 to the left of a peak emission 108; the trailing spectral edge 106 is a portion of the emission spectrum 102 to the right of the peak emission 108. Though the emission spectrum 102 is shown, the spectrum can also be an excitation spectrum.

FIG. 1B shows an emission spectrum 110 of a second detection moiety. The emission spectrum 110 includes a leading spectral edge 112 and a trailing spectral edge 114. In other words, the leading spectral edge 112 is a portion of the emission spectrum 110 to the left of a peak emission 116; the trailing spectral edge 114 is a portion of the emission spectrum 110 to the right of the peak emission 116. Though the emission spectrum 110 is shown, the spectrum can also be an excitation spectrum.

Figure 1C:
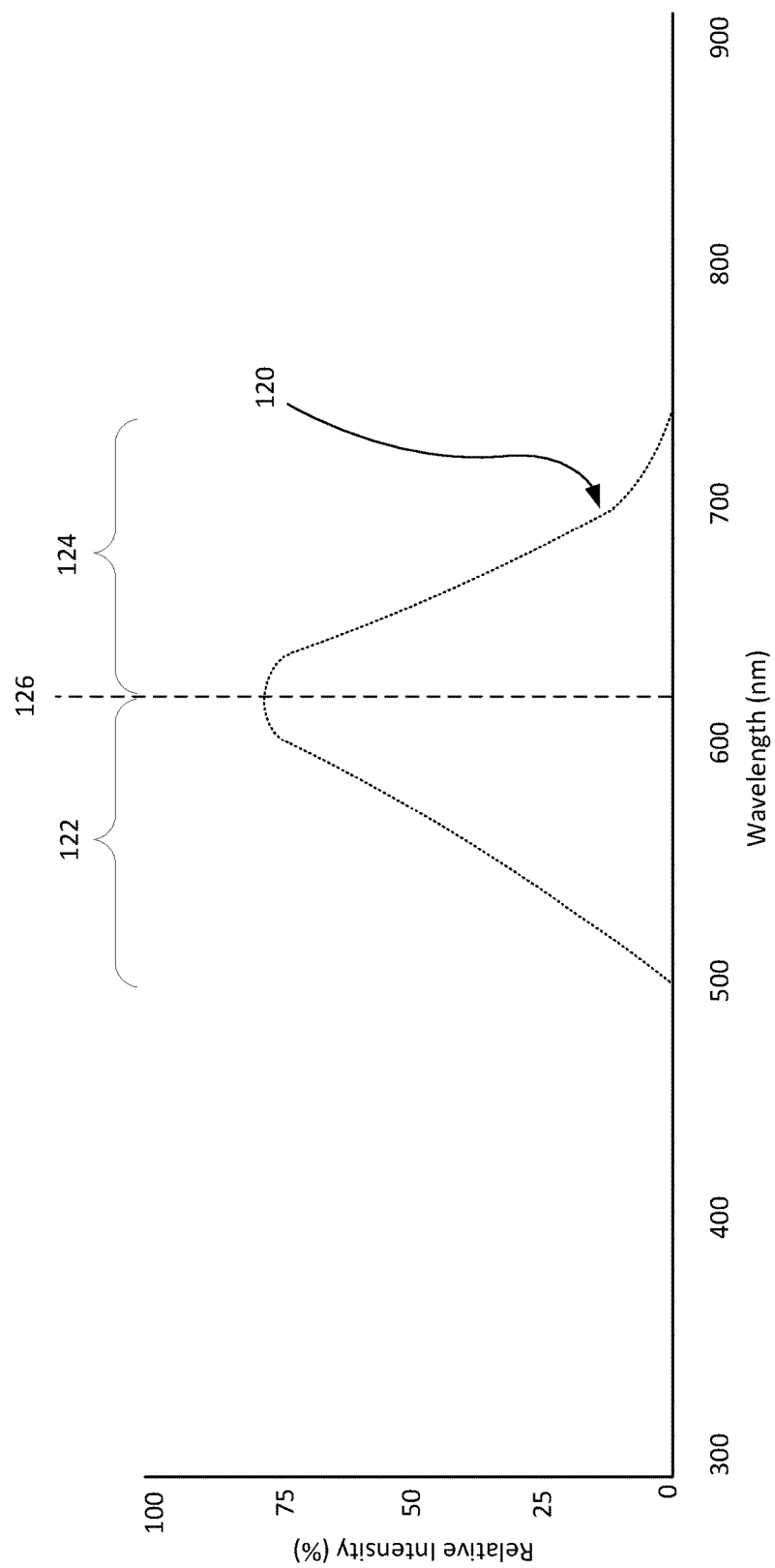
FIG. 1C shows an example third emission spectrum.

FIG. 1C shows an emission spectrum 120 of a third detection moiety. The emission spectrum 120 includes a leading spectral edge 122 and a trailing spectral edge 124. In other words, the leading spectral edge 122 is a portion of the emission spectrum 120 to the left of a peak emission 126; the trailing spectral edge 124 is a portion of the emission spectrum 120 to the right of the peak emission 126. Though the emission spectrum 120 is shown, the spectrum can also be an excitation spectrum.

In one embodiment, any of the methods or systems can be used to detect a stain or detection while removing background or autofluorescence from an image or a signal. For example, two or more raw images of a first detection moiety are provided, such that at least one of the images is at a lower end of a spectral edge of the first detection moiety and at least one the images is at a higher end of the spectral edge of the first detection moiety. At least one of the raw images includes a signal caused by autofluorescence or background. A first final image of the first detection moiety is provided, such that the first final image based on the raw images from the first detection moiety, and the first final image does not include the signal caused by the autofluorescence or background. This can be performed for any number of detection moieties to remove background or autofluorescence from any images.

Figure 2B:
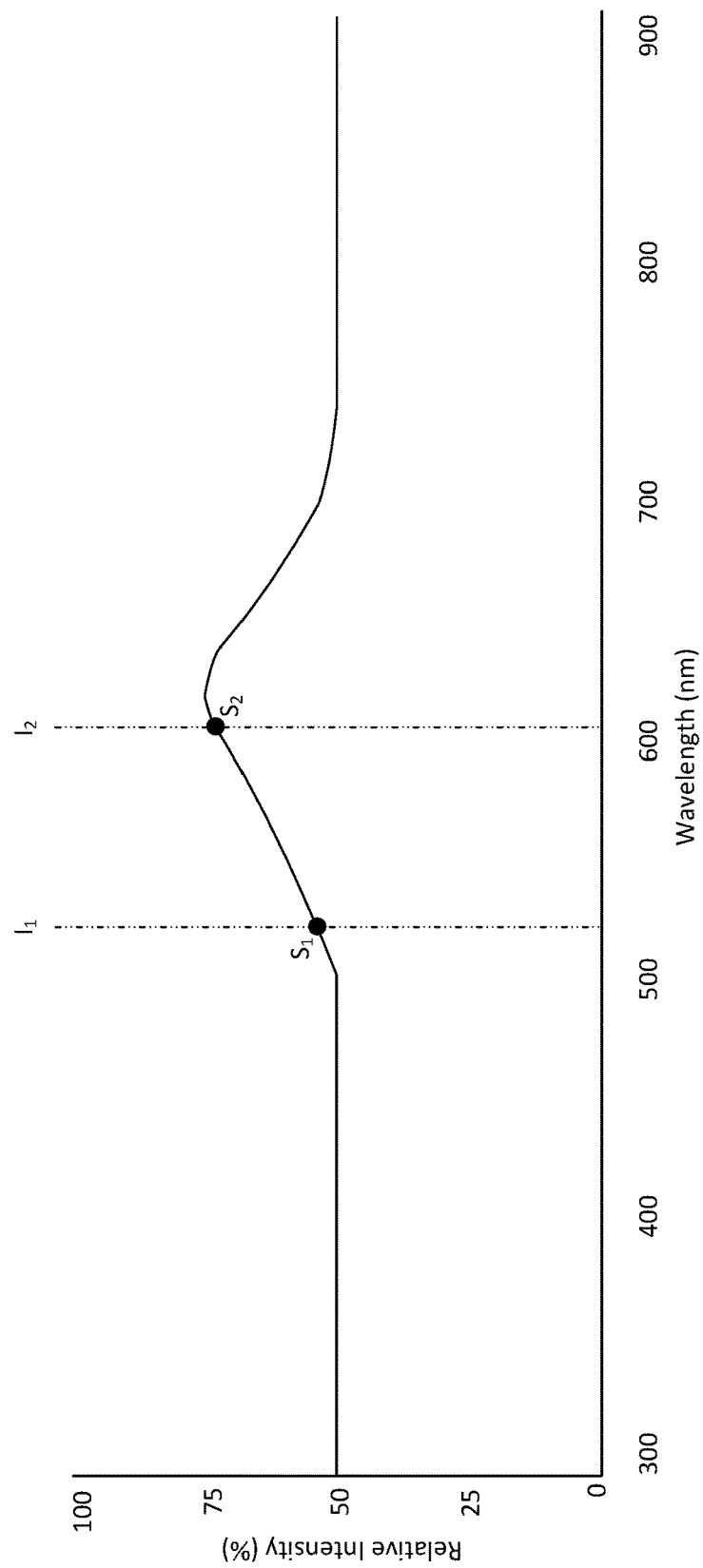
FIG. 2B shows a signal obtained during imaging.

In FIGS. 2A and 2B, a fourth detection moiety (as depicted by emission spectrum 204) is used as an example for the method by which an individual detection moiety is distinguished over background or autofluorescence. It should be noted, however, that the method discussed herein is not so limited and can also be implemented on the first, second, and/or third detection moieties (as depicted by emission spectra 102, 110, 120) or any other appropriate detection moiety.

FIG. 2A shows the emission spectrum 204 and a background signal 202. The background signal 202 is expected to be relatively unvarying with respect to the signal of interest and therefore depicted as a constant (i.e., a straight line) with a known value. Additionally, the relative intensities between the emission spectrum 204 and the background signal 202 are unknown.

For clarification purposes, FIGS. 2B-3D depict images $I_1$-$I_{14}$ obtained from of a single wavelength. However, the images $I_1$-$I_{14}$ can obtained across a given bandwidth (i.e., up to 1, 2, 3, 4, 5, 6, 7, 8, 9, 10, 11, 12, 15, 20, 25, 30, 40, 50, 60, 70, 75, 80, 90, 100, 150, 200, or more nm), such that the images (as denoted by the dot-dot-dash lines) denote the average signal across the respective bandwidths.

FIG. 2B shows raw images $I_1$ and $I_2$ including first and second signals S1 and $S_2$, respectively, obtained during imaging. The signals $S_1$ and $S_2$ denote the total contributions of the fourth detection moiety and the background 202. Raw image $I_1$ includes the first signal $S_1$ on a lower end of the leading spectral edge; and raw image $I_2$ is taken at a higher end of the leading spectral edge. To identify the fourth detection moiety (as shown by the emission spectrum 204), the raw images $I_1$ and $I_2$, are analyzed and the relative contribution of the fourth detection moiety between first and second signals $S_1$ and $S_2$ is determined by processing, comparing, and/or analyzing the change in signal with any appropriate mathematical, computational, or algebraic process or transformation, including, without limitation, subtraction, derivatives, or combinations thereof. A final image can then be provided depicting the fourth detection moiety based on the processing, comparing, and/or analyzing.

Spectral edge detection can be implemented for each detection moiety within the plurality of detection moieties, thereby allowing for multiplexing of a sample or fraction thereof with any desired number of detection moieties. In one embodiment, at least two detection moieties can be used for multiplexing. In one embodiment, any appropriate number of detection moieties can be used, including 2, 3, 4, 5, 6, 7, 8, 9, 10, 11, 12, 16, 20, 24, 28, 30, 32, 40, 50, 60, 70, 80, 90, or 100. In one embodiment, any appropriate number of detection moieties can be used, including up to 2, 3, 4, 5, 6, 7, 8, 9, 10, 11, 12, 16, 20, 24, 28, 30, 32, 40, 50, 60, 70, 80, 90, or 100. In one embodiment, any appropriate number of detection moieties can be used, including less than 3, 4, 5, 6, 7, 8, 9, 10, 11, 12, 16, 20, 24, 28, 30, 32, 40, 50, 60, 70, 80, 90, or 100.

Spectral edge detection can be implemented for detection moieties having spectral offsets, where the spectral offsets are spectral differences on the comparable spectral edge or at the spectral peaks. In one embodiment, this process can be implemented for detection moieties having differences in spectral offsets of less than or equal to 50 nm. In one embodiment, this process can be implemented for detection moieties having differences in spectral offsets of less than or equal to 10 nm. In one embodiment, this process can be implemented for detection moieties having differences in spectral offsets of 1-50 nm. In one embodiment, this process can be implemented for detection moieties having differences in spectra of 10-50 nm. In one embodiment, this process can be implemented for detection moieties having differences in spectral offsets of 1, 2, 3, 4, 5, 6, 7, 8, 9, 10, 11, 12, 15, 20, 25, 30, 40, 50, 60, 70, 75, 80, 90, or 100 nm. In one embodiment, the difference between successive spectra (such as at the peak) can be the same (e.g., first and second detection moieties are separated by 10 nm and second and third detection moieties are separated by 10 nm). In one embodiment, the differences between successive spectra (such as at the peak) can be different (e.g., first and second detection moieties are separated by 10 nm and second and third detection moieties are separated by 25 nm).

In one embodiment, the signal contributions of each detection moiety (for example, by way of the contribution or subtraction coefficients) can be determined with at least two raw images, such as by cancelling out or nullifying the signal contributions provided by the non-interested detection moiety (i.e., a first detection moiety is the non-interested detection moiety and a second detection moiety is the detection moiety of interest; and/or, then the first detection moiety is the detection moiety of interest and the second detection moiety is the non-interested detection moiety) or background/autofluorescence. Any number of raw images equal to or greater than 2 can be obtained for spectral edge detection, including, without limitation, 3, 4, 5, 6, 7, 8, 9, 10, 11, 12, 15, 20, 25, 30, 40, 50, 60, 70, 75, 80, 90, 100, or more.

For clarity purposes regarding FIGS. 3A-3D, the emission spectrum 102 of the first detection moiety is also designated by "A"; the emission spectrum 110 of the second detection moiety is also designated by "B"; and, the emission spectrum 120 of the third detection moiety is also designated by "C." The subscripts following A, B, or C in this description designate the image to which the detection moiety of interest is contributing intensity. For example, a data point $A_3$ denotes the contribution of A (or, the first detection moiety) within raw image $I_3$, as shown by the data point $A_3$ on the emission spectrum 102. So, $A_3$-$A_{14}$ denote the contributions of A (or, the first detection moiety) in raw images $I_3$-$I_{14}$, respectively; $B_3$-$B_{14}$ denote the contributions of B (or, the second detection moiety) in raw images $I_3$-$I_{14}$, respectively; and, $C_3$-$C_{14}$ denote the contributions of C (or, the third detection moiety) in raw images $I_3$-$I_{14}$, respectively.

Figure 3A:
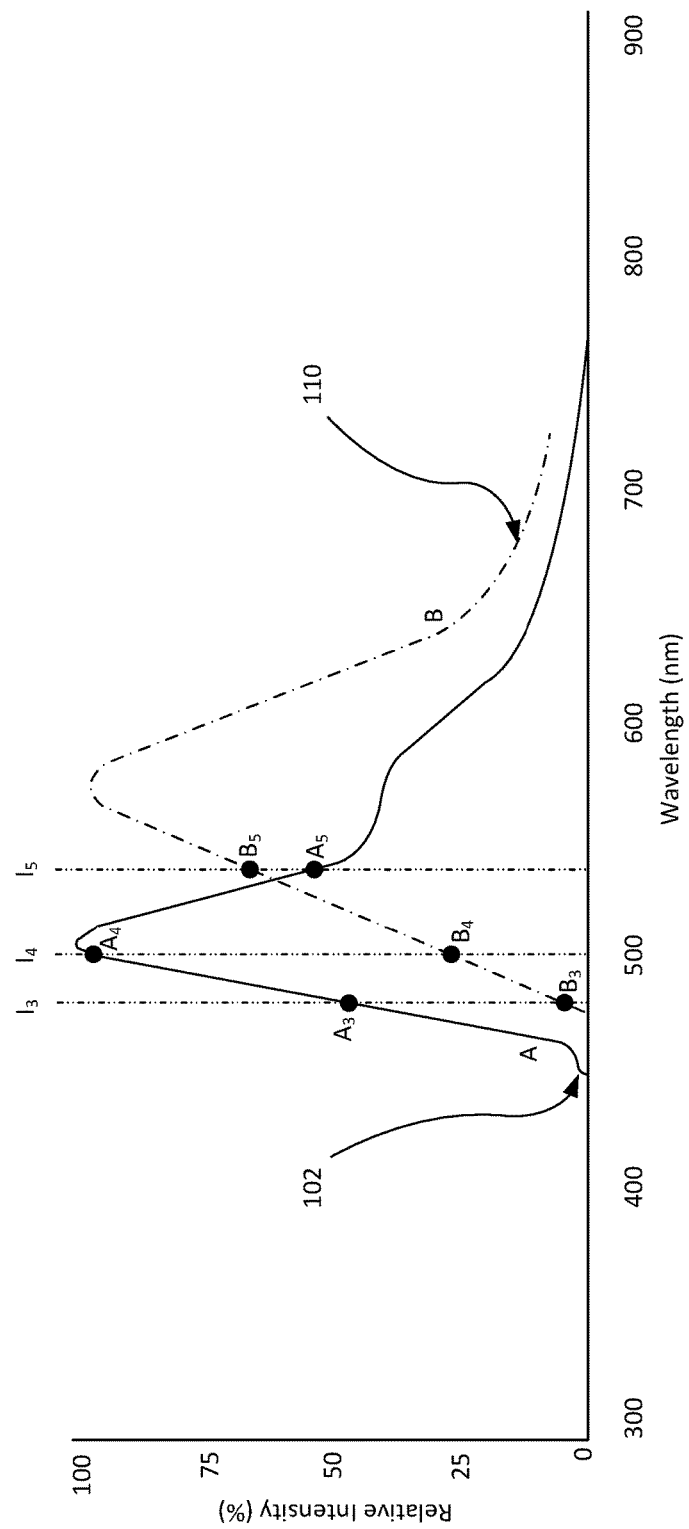
FIGS. 3A-3C show the example first and second emission spectra.

FIG. 3A shows the emission spectra 102, 110 for the first and second detection moieties. Raw images $I_3$, $I_4$, and $I_5$ are obtained. Raw image $I_3$ is taken at a lower end of the leading spectral edge 104; raw image $I_4$ is taken at a higher end of the leading spectral edge 104, which also overlaps with a lower end of the leading spectral edge 112; and, raw image $I_5$ is taken at a higher end of the leading spectral edge 112. Though the emission spectra 102, 110 are shown, the specta can also be excitation spectra.

In one embodiment, more than three raw images can be obtained. In one embodiment, each of the raw images are used to analyze one and only one of the detection moieties. In one embodiment, one or more of the raw images are used to analyze at least two of the detection moieties (i.e., there is an overlap). In one embodiment, none of the raw images between the first and second detection moieties are the same (i.e. all images are distinct). In one embodiment, at least one of the raw images of the first detection moiety and at least one of the raw images of the second detection moiety is the same image.

In one embodiment, a raw image taken at the higher end of the trailing spectral edge can include the higher end of the leading spectral edge, and vice-versa (i.e., a raw image taken at the higher end of the leading spectral edge can include the higher end of the trailing spectral edge). In one embodiment, a raw image taken at the higher end of the particular spectral edge does not include the higher end of the opposing spectral edge (i.e., raw image at higher trailing spectral edge does not include higher leading spectral edge; raw image at higher leading spectral edge does not include higher trailing spectral edge).

To identify a first detection moiety (as shown by the emission spectrum 102) and a second detection moiety (as shown by the emission spectrum 110), the raw images $I_3$, $I_4$, and $I_5$ are analyzed and the relative contributions of the first and second detection moieties are determined. For example, the relative contributions can be determined by any appropriate mathematical, computational, or algebraic process or transformation, including, without limitation, subtraction, derivatives, or combinations thereof. A final image of the first detection moiety is then provided based on the analysis of raw images $I_3$, $I_4$, such as the relative contribution of the first detection moiety across the raw images $I_3$, $I_4$. A final image of the second detection moiety is then provided based on the analysis of raw images $I_4$, $I_5$, such as the relative contribution of the second detection moiety across the raw images $I_4$, $I_5$.

Figure 3B:
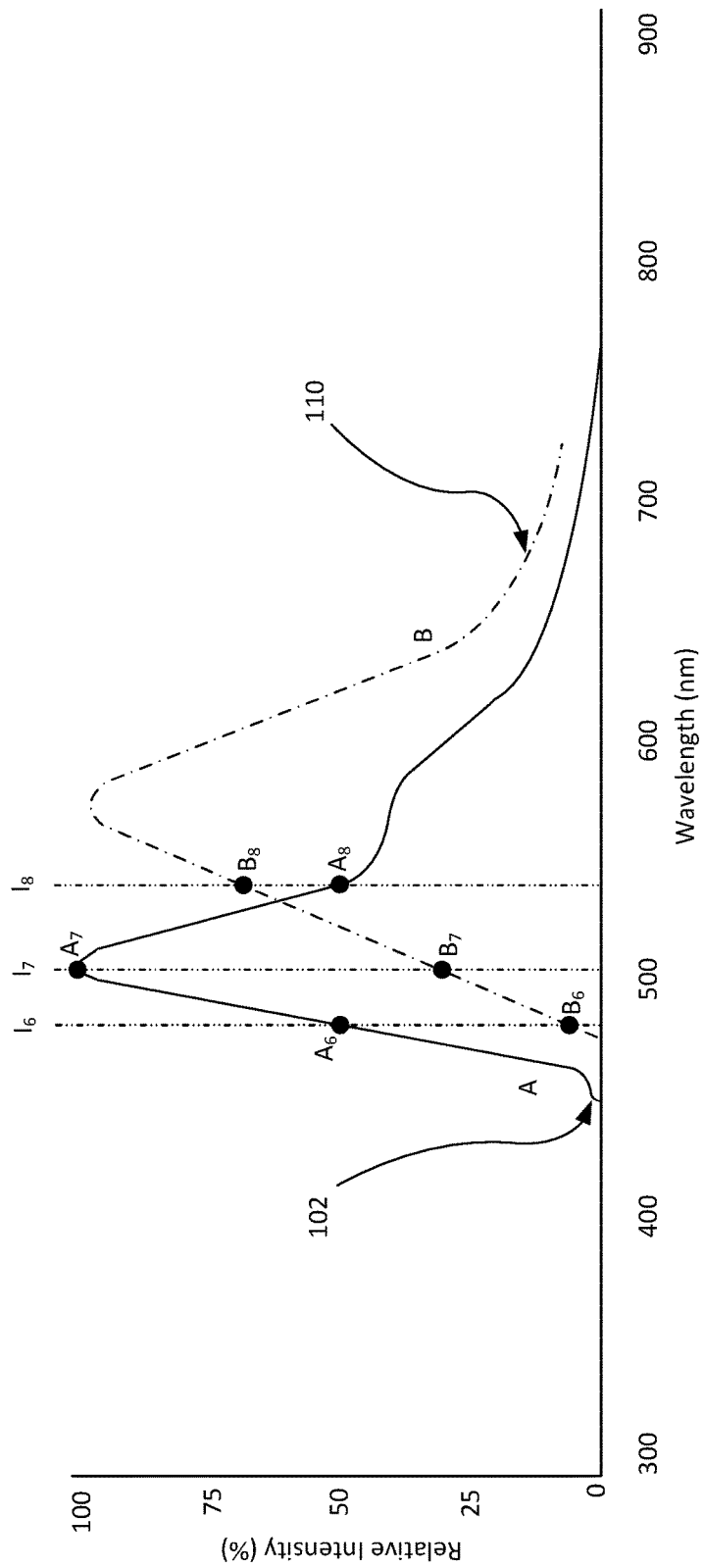

FIG. 3B shows the example first and second emission spectra similar to that of FIG. 3A, except having obtained raw images $I_6$, $I_7$, and $I_8$. Raw images $I_6$ and $I_8$ are taken at points where the emission intensity of the first detection moiety has the same or substantially the same value and the emission intensity of the second detection moiety is different between the images. Raw image $I_7$ is take at a point such that the at least three data points for the second detection moiety form a line.

Figure 3C:
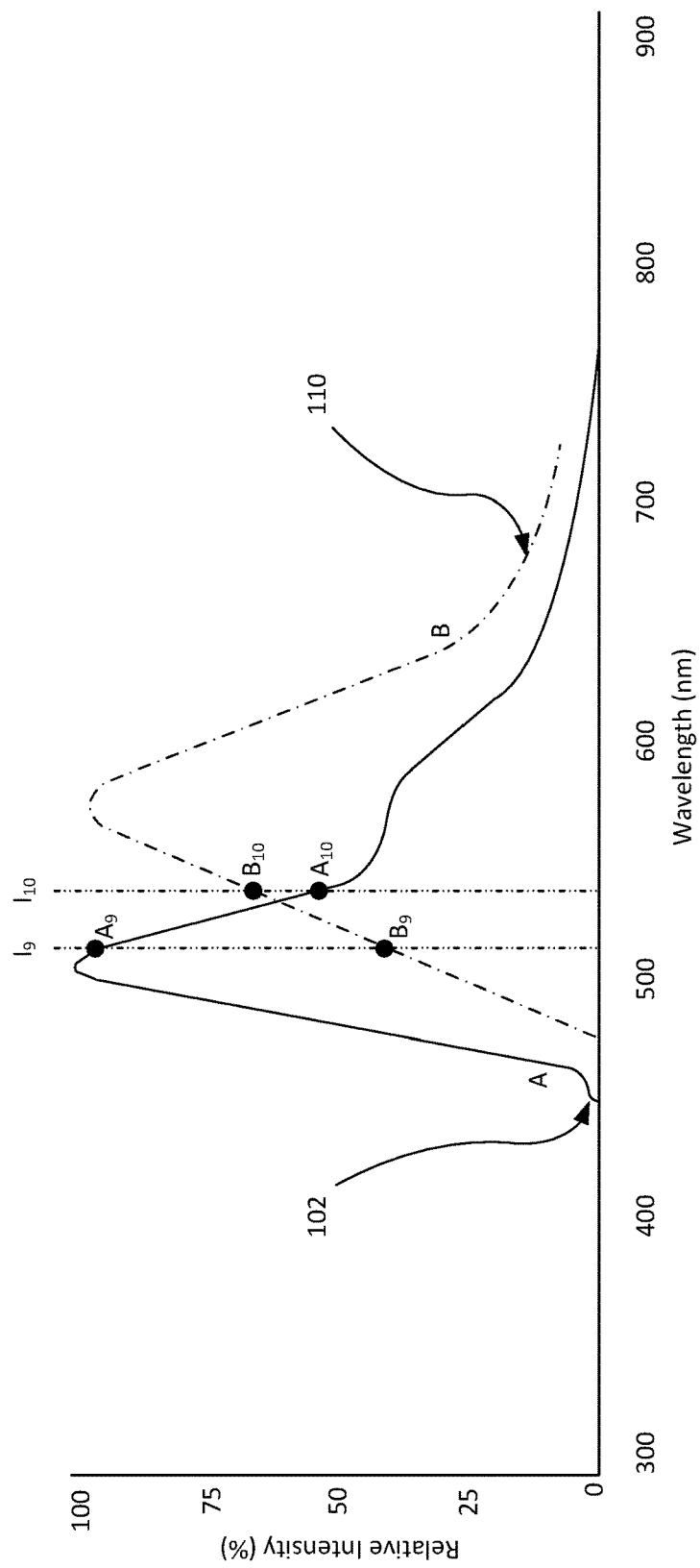

FIG. 3C shows the example first and second emission spectra similar to that of FIG. 3A, except having obtained raw images $I_9$ and $I_{10}$. Raw images $I_9$ and $I_{10}$ are taken at points where a higher end of a spectral edge of the first detection moiety overlaps with a lower end of a different spectral edge of the second detection moiety, and where a lower end of the spectral edge of the first detection moiety overlaps with a higher end of the different spectral edge of the second detection moiety. As shown in FIG. 3C, the trailing edge of the first detection moiety overlaps with the leading edge of the second detection moiety such that raw image $I_9$ includes the higher end of the trailing spectral edge of the first detection moiety and the lower end of the leading spectral edge of the second detection moiety, and raw image $I_{10}$ includes the lower end of the trailing spectral edge of the first detection moiety and the higher end of the leading spectral edge of the second detection moiety. In one embodiment, the leading edge of the first detection moiety overlaps with the trailing edge of the second detection moiety.

In one embodiment, two or more raw images of a first emission spectrum are obtained, wherein at least one of the images is at a lower end of a spectral edge of the first emission spectrum and at least one the images is at a higher end of the same spectral edge of the first emission spectrum. Two or more raw images of a second emission spectrum are obtained, wherein at least one of the images is at a lower end of a spectral edge of the second emission spectrum and at least one the images is at a higher end of the same spectral edge of the second emission spectrum. A first final image of a first detection moiety (as depicted by the first emission spectrum) and a second final image of a second detection moiety (as depicted by the second emission spectrum) are provided, wherein the first and second final images are based on the raw images from the first and second detection moieties. In one embodiment, at least one of the raw images of the first and second emission spectra is the same image. For example, the second image of the first emission spectrum (at the higher end of the first emission spectrum's spectral edge) is the same image as the first image of the second emission spectrum (at the lower end of the second emission spectrum's spectral edge).

Though two detection moieties are discussed, this process can be used for any number of detection moieties. In other words, two or more raw images of a $n^{th}$ emission/excitation spectrum are obtained, wherein at least one of the images is at a lower end of a spectral edge of the $n^{th}$ emission/excitation spectrum and at least one the images is at a higher end of the spectral edge of the $n^{th}$ emission/excitation spectrum, and wherein n is greater than or equal to 1 (i.e., 1, 2, 3, 4, 5, 6, 7, 8, 9, 10, 11, 12, 16, 20, 24, 28, 30, 32, 40, 50, 60, 70, 80, 90, 100, or more). This process is then repeated for at least one more emission/excitation spectrum.

In one embodiment, to determine signal contribution by individual detection moieties having overlapping spectra, at least three data points of one detection moiety are to be obtained, such that the three data points form a curve; and, at least two data points of another detection moiety are to be obtained, such that the two data points form a line. The determination as to which detection moiety requires the data points to form the curve or the data points to form the line are based on the relative spectral edges. In other words, when using the same spectral edge (i.e., leading or trailing) of different emission spectra, the emission spectrum having at least a portion of the same spectral edge fall under the emission spectrum of the other emission spectrum only requires at least two data points. The at least two data points (i.e., those forming the line) can be used to determine the contribution of the detection moiety whether in the presence or absence of the curve provided by the other detection moiety; and, additionally, the at least three data points (i.e., those forming the curve) can be used to determine the contribution of the other detection moiety whether in the presence or absence of the line provided by the initial detection moiety.

Figure 3D:
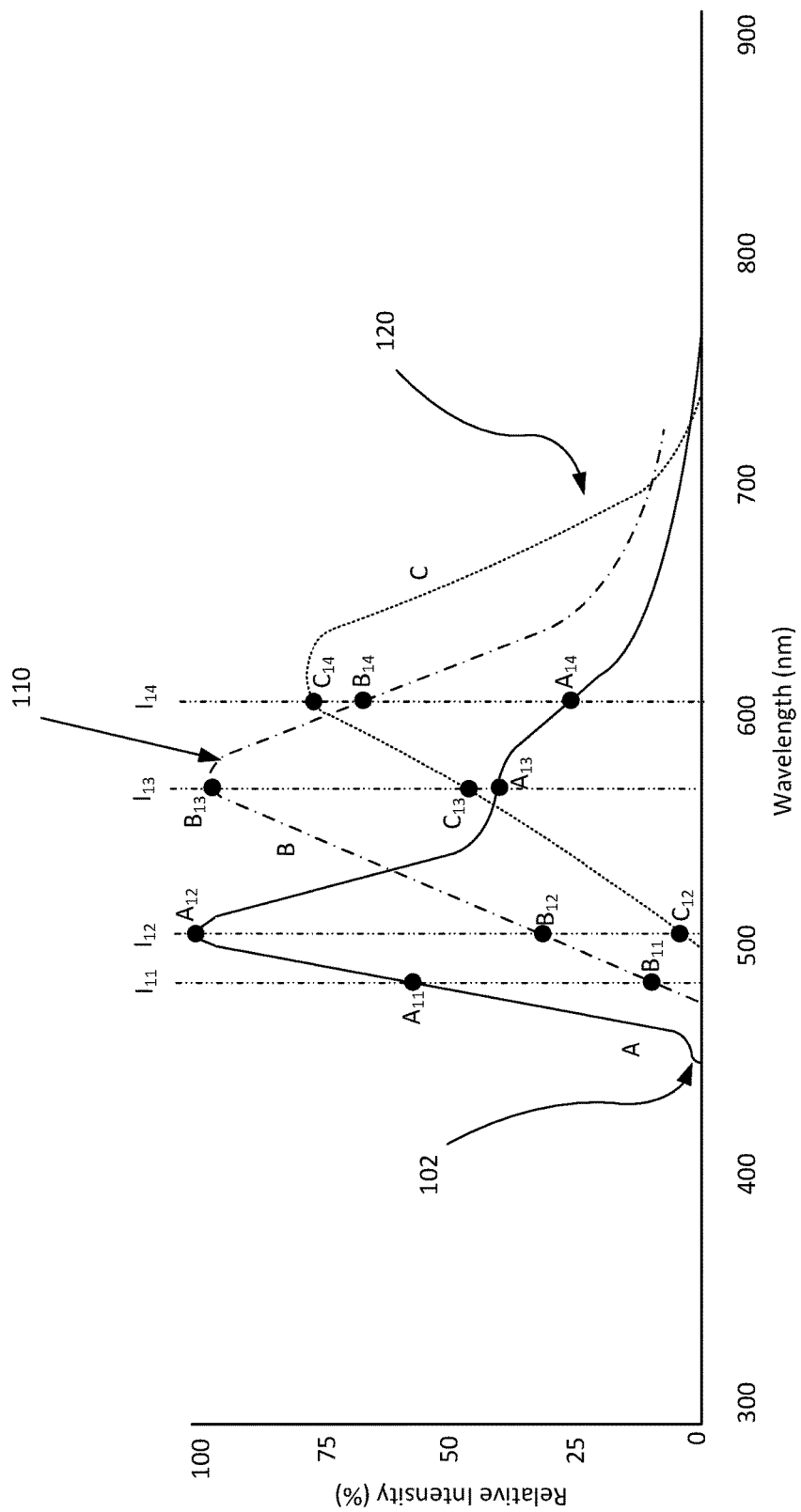
FIG. 3D shows the example first and second emission spectra and a third emission spectrum.

FIG. 3D depicts three emission spectra 102, 110, 120 (A, B, C) within four images $I_{11}$-$I_{14}$. A leading edge of emission B is underneath a leading edge of emission A. Therefore, at least three data points are obtained for emission A (e.g., $A_{11}$-$A_{13}$; or, $A_{11}$, $A_{12}$, $A_{14}$), and at least two data points are obtained for emission B (e.g., $B_{11}$ and $B_{12}$; or, $B_{11}$ and $B_{13}$; or, $B_{12}$ and $B_{13}$). Additionally, a leading edge of emission C is underneath a leading edge of emission B. Therefore, at least three data points are obtained for emission B (e.g., $B_{11}$, $B_{13}$, $B_{14}$; or, $B_{12}$-$B_{14}$), and at least two data points are required for emission C (e.g., $C_{12}$ and $C_{13}$; or, $C_{13}$ and $C_{14}$; or, $C_{12}$ and $C_{14}$). The respective data points for the emissions A-C can be used to determine the respective contributions of the detection moieties.

In one embodiment, change in signal intensity (i.e., pixel levels) can be used to identify a detection moiety.

In one embodiment, such as when representative points of the emission spectrum are obtained, the rate of change or the change in signal intensity can be determined based on the trailing edge of the spectrum. In one embodiment, such as when representative points of the emission spectrum are obtained, the rate of change or the change in signal intensity can be determined based on the leading edge of the spectrum.

In one embodiment, such as when representative points of the excitation spectrum are obtained, the rate of change or the change in intensity can be determined based on the trailing edge of the spectrum. In one embodiment, such as when representative points of the excitation spectrum are obtained, the rate of change or the change in intensity can be determined based on the leading edge of the spectrum.

In one embodiment, the change in signal intensity can be compared against an expected value. For example, the change in intensity can be the expected value +/− (plus or minus) up to 0.01%, 0.02%, 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 2%, 5%, 10%, 15%, 20%, 25%, 30%, 33%, 35%, 40%, 45%, 50%, 55%, 60%, 65%, 70%, 75%, 80%, 85%, 90%, 95%, or 99%. In one embodiment, the change in signal intensity can be compared against a threshold. In one embodiment, the change in signal intensity can be positive or negative, such that the positive or negative change identifies the desired detection moiety.

In one embodiment, a threshold can be applied, such as during image processing and analysis, to determine whether the signal is caused by the desired detection moiety, an undesired detection moiety, noise, or background.

In one embodiment, when a change in signal intensity between the first and second images, such as at a desired or pre-determined wavelength, is equal to or greater than a first threshold value, the pixel or signal is "kept on" for the resulting image for analysis; whereas when a change in signal between the first and second images is less than the first threshold value, the pixel or signal is "turned off" for the resulting image for analysis.

In one embodiment, a first emission derivative of the emission spectrum 102 of the first detection moiety can be obtained; and, a second emission derivative of the emission spectrum 110 of the second detection moiety can be obtained. Though a first-order derivative is discussed, any higher-order derivative can be calculated when it is desirous to do so.

In one embodiment, such as when representative points of the emission spectrum are obtained, the rate of change can be greater than or equal to a threshold value. In one embodiment, such as when representative points of the emission spectrum are obtained, the change in intensity can be positive, positive by at least a threshold amount, and/or positive by a certain multiple of the first emission. In one embodiment, such as when representative points of the excitation spectrum are obtained, the rate of change can be less than or equal to a threshold value (i.e. more negative— for example −5 is less than −3). In one embodiment, such as when representative points of the excitation spectrum are obtained, the change in intensity can be negative, negative by at least a threshold amount, and/or negative by a certain multiple of the first excitation.

As an example, $\Delta x$ (the change in emission wavelength) is 10 nm and $\Delta y$ (the change in emission intensity) is 50%, the slope is 50%/10 nm, or 5%/nm. When comparing the first and second images, an increase of intensity of at least 5 times between respective pixels can be attributed to the first detection moiety and the pixel is "kept on"; whereas an increase of intensity of less than 5 times between respective pixels can be attributed to something other than the first detection moiety (e.g., background) and the pixel is "turned off." The example is not intended to be limited to values and/or percentages. The first threshold value can include a range based on the anticipated or expected change of emission intensity. For example, the first threshold value can be the slope +/− (plus or minus) up to 0.01%, 0.02%, 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 2%, 5%, 10%, 15%, 20%, 25%, 30%, 33%, 35%, 40%, 45%, 50%, 55%, 60%, 65%, 70%, 75%, 80%, 85%, 90%, 95%, or 99%.

The slope satisfies the condition given by:

$$\text{slope} = \frac{\text{intensity of the second emission} - \text{intensity of the first emission}}{\text{wavelength of the second emission} - \text{wavelength of the first emission}}.$$

In one embodiment, when exciting the first detection moiety (and thereby obtaining a first image), a wavelength of a first excitation light can be selected to not excite the second detection moiety. Then, a wavelength of a second excitation light can also be selected to excite the first detection moiety (thereby providing a second image) and to not excite the second detection moiety. The first and second images can be processed and compared to obtain the change of emission intensity (in other words, the slope, or y/x) based on the emissions of the first detection moiety due to the change in excitation wavelengths.

In one embodiment, at least one of the excitation lights can stimulate one or more detection moieties. However, the resulting slopes, as discussed below, can be used to remove the signal of one or more non-desired detection moieties.

In one embodiment, two or more images, resulting from the two or more excitation wavelengths can be compared and processed to calculate the desired slope. The resulting slope can be used to keep the signal on or turn the signal off in a final image. In one embodiment, two or more signals, resulting from the two or more excitation wavelengths can be compared and processed to calculate the desired slope. The resulting slope can be used to keep the signal on or turn the signal off in a final image.

In one embodiment, any of the methods or systems can be used for a plurality of stains on or within a sample or fraction thereof. The steps can be performed simultaneously for at least two of the stains or can be performed for a first stain and then for a second stain. In one embodiment, the first- or higher-order derivative can be calculated for each detection moiety spectral edge. In one embodiment, the spectral edge of the respective detection moieties can be used to differentiate between the emissions of the different detection moieties.

In one embodiment, the minimum number of raw images is n, where n is the number of detection moieties. For example, a first raw image can be obtained at a higher end of a trailing edge of a first emission spectrum and at a lower end of a leading edge of a second emission spectrum. A second raw image can be obtained at a lower end of the trailing edge of the first emission spectrum and at a higher end of the leading edge of the second emission spectrum. The first and second raw images can be processed and/or analyzed to provide a first final image of a first detection moiety (as depicted by the first emission spectrum) and a second final image of a second detection moiety (as depicted by the second emission spectrum). Though the emission spectra is discussed, this embodiment can be implemented on excitation spectra.

In one embodiment, the minimum number of raw images is n+1, where n is the number of detection moieties.

In one embodiment, all of the raw and final images of the first and second detection moieties are displayed to an end user or operator, such as on a screen (e.g., the screen of at least one of a phone, a tablet, a computer, a television, a PDA, a handheld device, or the like). In one embodiment, at least one of the raw images of the first and/or second detection moieties is displayed. In one embodiment, at least one of the final images of the first and/or second detection moieties is displayed. In one embodiment, none of the raw images are displayed but at least one of the final images is displayed. In one embodiment, none of the raw images are displayed but all of the final images are displayed.

Figure 4A:
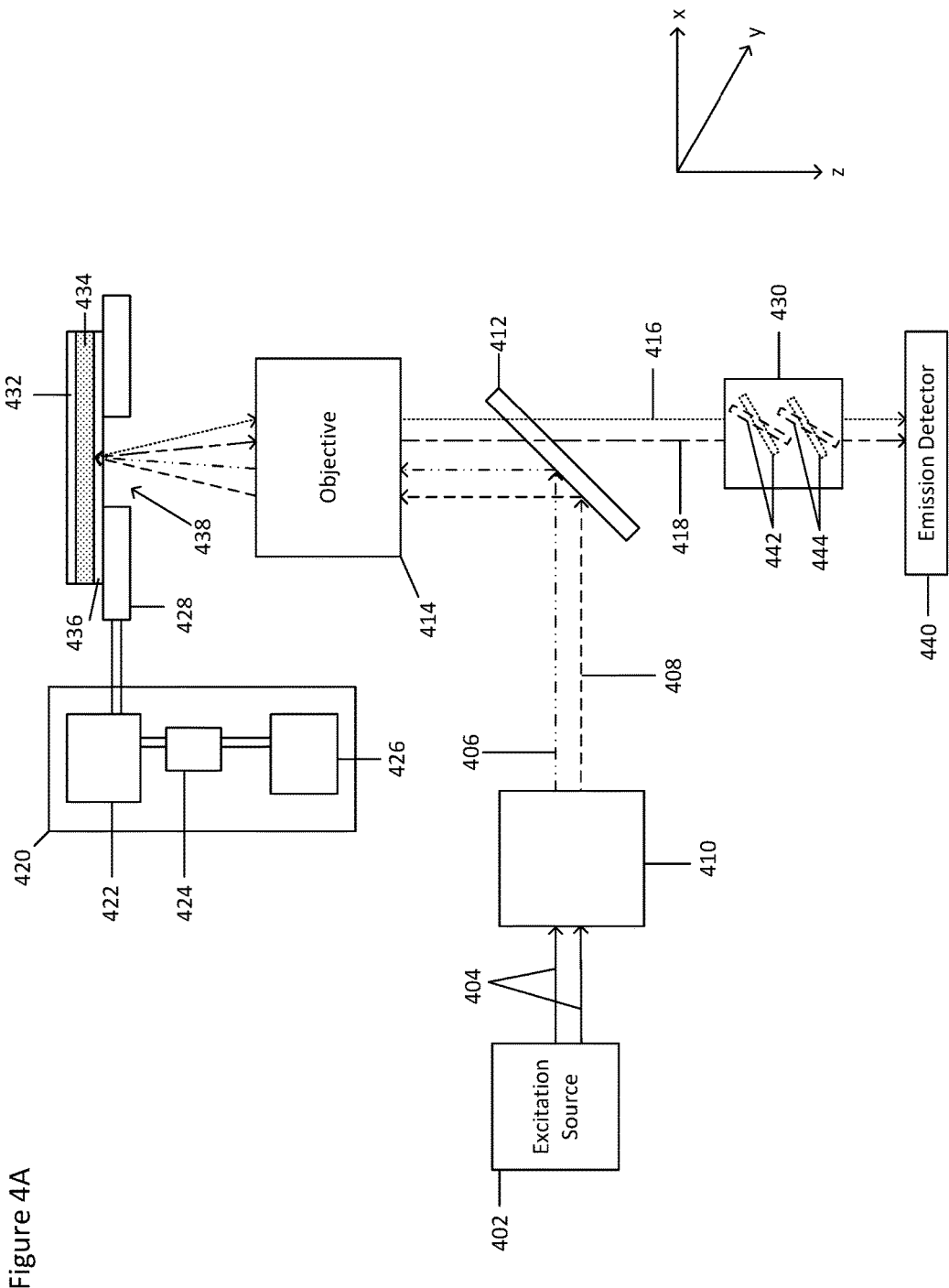
FIG. 4A shows an example optical path of a fluorescent microscope.

To obtain the raw images, the imaging can be done with a flow cytometer or a microscope, such as a fluorescent microscope, a scanner, or the like. Imaging can be done in, conventional epifluorescence, light sheet microscopy, super resolution microscopy, and confocal microscopy. FIG. 4A shows an optical path of a fluorescent microscope. The optical path includes an excitation source 402 which emits an excitation light 404, such as a light in the visible, infrared ("IR"), or ultraviolet ("UV") spectra. The excitation light 404 comprises a plurality of wavelengths, including at least a first excitation wavelength 406 and a second excitation wavelength 408. The excitation light 404 interacts with an excitation spectrum selector 410, such that the first excitation wavelength 406 passes through the excitation spectrum selector 410 and the second excitation wavelength 408 is blocked from passing through the excitation spectrum selector 410. The first excitation wavelength 406 is then reflected off a second filter 412. The second filter 412 re-directs the first excitation light 406 into an objective 414.

The objective 414 receives the first excitation wavelength 406 and focuses the first excitation wavelength at a point or surface on, within, or near a sample or fraction thereof 434. The first excitation wavelength 406 stimulates a first detection moiety (not shown) on or with the sample or fraction thereof 434, thereby causing the first detection moiety (not shown) to emit a first emission light 416 having a first emission wavelength. The first emission light 416 can be captured by the objective 414, passed back through the second filter 412, passed through an emission spectrum selector 430, and onto an emission detector 440. The emission detector 440 can be a charge-coupled device ("CCD"), CMOS camera, a scientific CMOS camera, photodiode, photomultiplier tube, or the like for capturing image data, which can then be compiled into images, processed and analyzed by a computer or associated software or programs.

The excitation source 402 emits the excitation light 404 again. The excitation light 404, however, now interacts with the excitation spectrum selector 410, such that the second excitation wavelength 408 passes through the excitation spectrum selector 410 and the first excitation wavelength 406 is blocked from passing through the excitation spectrum selector 410. The second excitation wavelength 408 is then reflected off the second filter 412. The second filter 412 re-directs the second excitation light 408 into the objective 414. The objective 414 receives the second excitation wavelength 408 and focuses the first excitation wavelength at a point or surface on, within, or near a sample or fraction thereof 434. The second excitation wavelength 408 stimulates the first detection moiety (not shown) on or with the sample or fraction thereof 434, thereby causing the first detection moiety (not shown) to emit a second emission light 418 having a second emission wavelength. The second emission light 418 can be captured by the objective 414, passed back through the second filter 412, passed through the emission spectrum selector 430, and onto an emission detector 440.

The process discussed can be performed any number of times for any number of detection moieties.

The second filter 412 can each be a dichroic, polychroic, bandpass, bandstop, or any appropriate filter.

The sample or fraction thereof 434 can be located on a base 432 or between a cover 436 and the base 432. The cover 436 and the base 432 can be optically clear to permit imaging. The sample 434, the cover 436, and the base 432 can be located on a platform 428 to move the sample 434 in an x-, y-, or z-direction as required. The platform 428 can include an aperture 438 which allows the first excitation wavelength 406, having been focused by the objective 414, into, on, or near the sample or fraction thereof 434. The platform 428 can be driven by a driver 420, which includes at least one of a z-direction drive 424, an x-direction drive 422, and a y-direction drive 426 to position the sample 434. The driver 420 can be a motor, such as a servomotor or a stepper motor, a piezo-electric actuator, a solenoid, or the like.

The optical path can also include a cut-off aperture (not shown), such as in a confocal microscope, to increase the signal/noise ratio of the boundary light signal.

The base 432 can be composed of glass; an inert metal; a metal; a metalloid; organic or inorganic materials, and plastic materials, such as a polymer; and combinations thereof. The cover 436 can be composed of an optically transparent material.

Figure 4B:
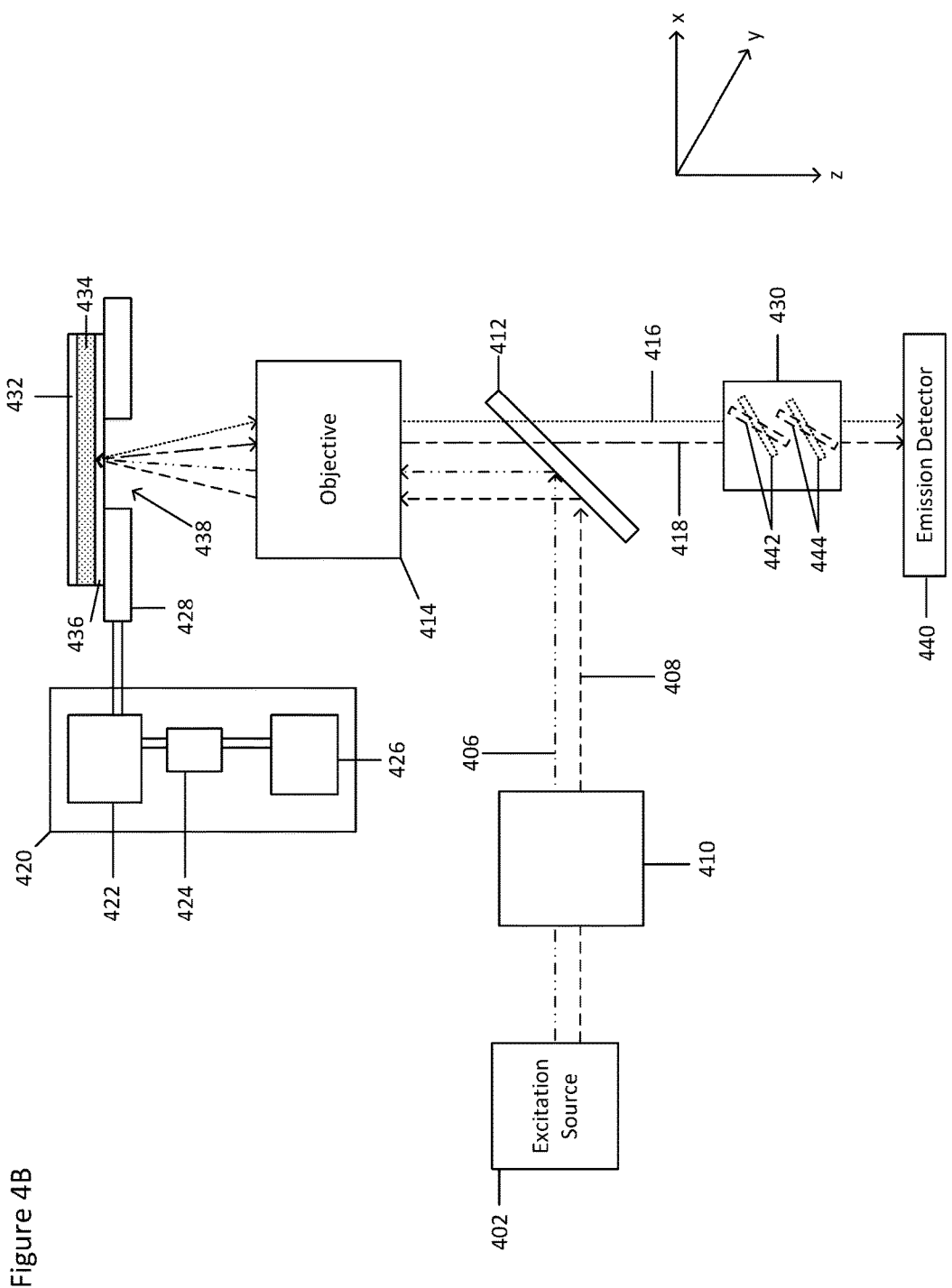
FIG. 4B shows an example optical path of a fluorescent microscope.

FIG. 4B shows an optical path of a fluorescent microscope similar to that of FIG. 4A, except that the excitation source 402 emits the first and second excitation wavelengths as separate lights 406, 408.

Figure 4C:
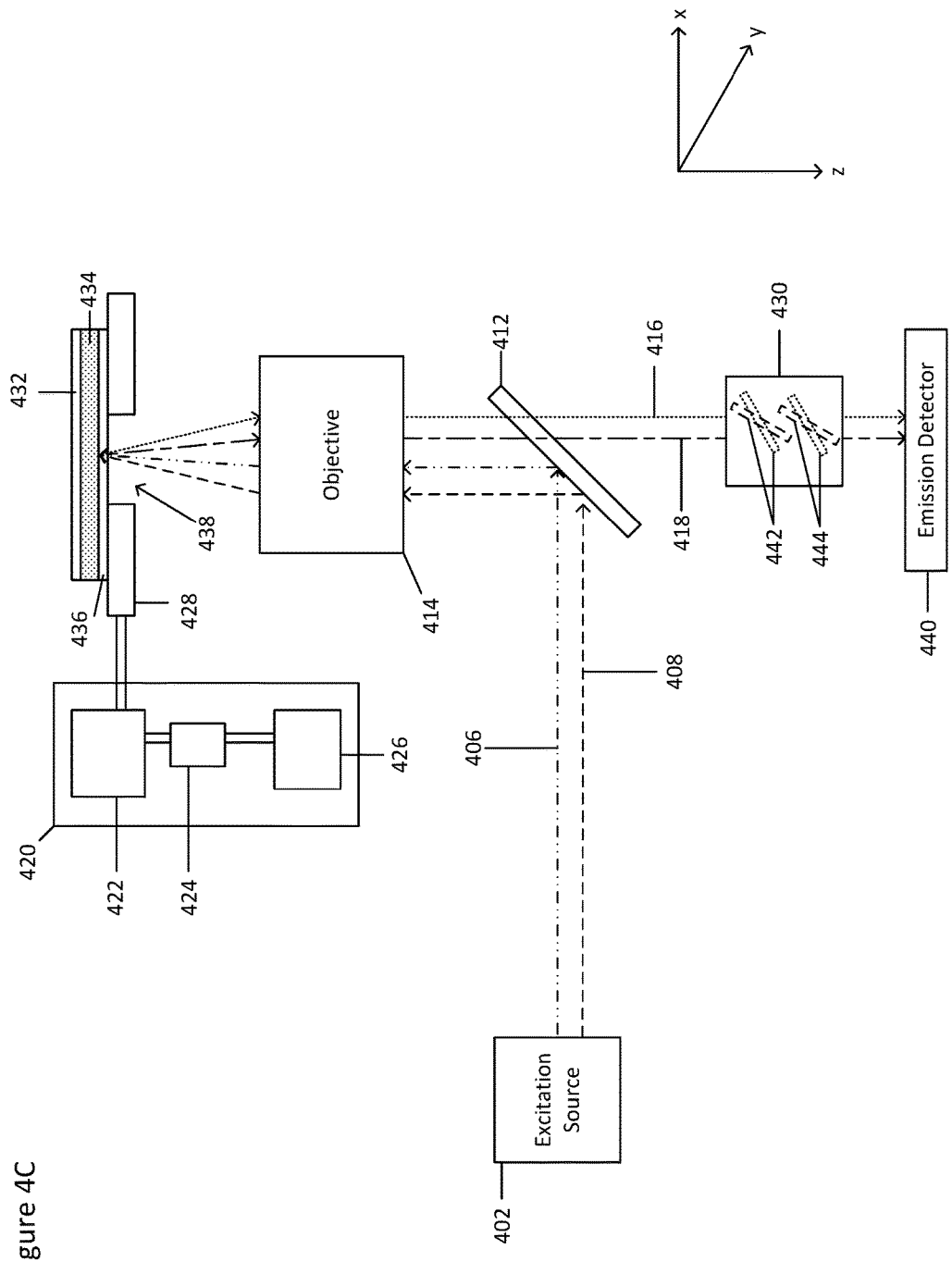
FIG. 4C shows an example optical path of a fluorescent microscope.

FIG. 4C shows an optical path of a fluorescent microscope similar to that of FIG. 4B, except that the excitation spectrum selector 410 is not incorporated into the optical path.

In one embodiment, the excitation spectrum selector 410 or the emission spectrum selector 430 can be a filter to block or pass given wavelengths. In one embodiment, the excitation spectrum selector 410 or the emission spectrum selector 430 can be a notch filter, a bandstop filter, or a bandpass filter. In one embodiment, the excitation spectrum selector 410 or the emission spectrum selector 430 can be a diffraction grating. In one embodiment, the excitation spectrum selector 410 or the emission spectrum selector 430 can include a filter capable of being re-angled to block or pass given wavelengths based on the angle at which the filter is tilted, turned, or adjusted relative to an incoming light, thereby changing the angle of incidence of light upon the filter. As an example, the first excitation wavelength 406 passes through the excitation spectrum selector 410 and the second excitation wavelength 408 is blocked from passing through the excitation spectrum selector 410 due to the angle of the excitation spectrum selector. Then, the excitation spectrum selector 410 can be re-angled ($\theta$) to block the first excitation wavelength 406 and pass the second excitation wavelength 408. Though the example discusses the excitation spectrum selector 410, the first excitation wavelength 406, and the second excitation wavelength 408, the optical pathway is not intended to be so limiting.

Re-angling can be applied to the emission spectrum selector 430 to block and pass certain emission wavelengths. Additionally, rotating or angling can be performed before or after capturing any raw image. In one embodiment, the emission spectrum selector 430 can include a first emission filter 442 capable of being rotated or angled from one angle of incidence (denoted by the longer dashed line filter 442) between the first filter 442 and the emission light to another angle of incidence (denoted by the shorter dashed line filter 442) between the first filter 442 and the emission light, including every angle in between. For example, a first raw image can be obtained with the first filter 442 at a first angle of incidence. Then the first filter 442 can be re-angled from the first angle of incidence to a second angle of incidence. A second raw image can then be obtained. Additionally, in capturing at least one more raw image, the first filter 442 can be re-angled from the second angle of incidence to a third angle of incidence. A third raw image can then be obtained. Additionally, in capturing at least one more raw image, the first filter 442 can be re-angled from the third angle of incidence to a fourth angle of incidence. A fourth raw image can then be obtained. In one embodiment, at least two of the first, second, third, and fourth angles are the same. In one embodiment, none of the first, second, third, and fourth angles are the same.

In one embodiment, the emission spectrum selector 430 can include two or more emission filters 442, 444 such that each one is capable of being rotated or angled. The first filter 442 can be rotated or angled from one angle of incidence (denoted by the longer dashed line filter 442) between the first filter 442 and the emission light to another angle of incidence (denoted by the shorter dashed line filter 442, 442) between the first filter 442 and the emission light, including every angle in between. The second filter 444 can be rotated or angled from a one angle of incidence (denoted by the longer dashed line filter 444) between the second filter 444 and the emission light to another angle of incidence (denoted by the shorter dashed line filter 444) between the second filter 444 and the emission light, including every angle in between. The first and second filters 442, 444 can be rotated or angled independently of each other. In other words, the first filter 442 can have any number of positions (i.e., first position, second position, third position, fourth position, and so on until the $n^{th}$ position) with each position corresponding to a different angle. The second filter 444 can have any number of positions (i.e., first position, second position, third position, fourth position, and so on until the $n^{th}$ position) with each position corresponding to a different angle. Each filter 442, 444 can have a position (or angle) independent of the other filter, such that one or both filters 442, 444 can be angled or rotated, and such that the filters 442, 444 can have the same angle of incident or difference angles of incidence. The filters 442, 444 can be positioned or angled to obtain desired wavelengths.

For example, a first raw image can be obtained with the first filter 442 at a first angle of incidence and the second filter 444 at a third angle of incidence. Then the first filter 442 can be re-angled from the first angle of incidence to a second angle of incidence, while the second filter 444 stays at the third angle of incidence. A second raw image can then be obtained. Additionally, in capturing at least one more raw image, the second filter 442 can be re-angled from the third angle of incidence to a fourth angle of incidence. A third raw image can then be obtained. In one embodiment, at least two of the first, second, third, and fourth angles are the same. In one embodiment, none of the first, second, third, and fourth angles are the same.

In any of the embodiments including rotating or angling at least one filter, any filter can be rotated or angled at any desired time or step to obtain a desired emission wavelength. For example, after obtaining a first raw image with the first and second filters 442, 444 at first and third angles of incidence, respectively, the first and second filters 442, 444 can be rotated or angled to second and fourth angles of incidence, respectively. A second raw image can then be obtained. Then, one or both of the filters 442, 444 can be rotated or angled. A third raw image can be obtained. In other words, each filter can be rotated or angled independently of the other filter or filters at any point and by any amount to obtain any raw image and/or any desired emission wavelength.

Furthermore, though one and two filters are discussed, any number of filters can be used, including, without limitation, 1, 2, 3, 4, 5, 6, 7, 8, 9, 10, 11, 12, 15, 20, 25, 30, 40, 50, 60, 70, 75, 80, 90, or 100.

Though the examples and embodiments discussed herein are applied to the emission spectrum selector 430, one or more filters capable of being rotated or angled, and the methods of using the same, can also be applied to the excitation spectrum selector 410. Accordingly, in one embodiment, at least one of the excitation and emission spectrum selectors 410, 430 can include at least one filter capable of being rotated or angled. In one embodiment, one of the excitation and emission spectrum selectors 410, 430 can include at least one filter capable of being rotated or angled. In one embodiment, both of the excitation and emission spectrum selectors 410, 430 can include at least one filter capable of being rotated or angled.

The individual filters of the excitation spectrum selector 410 or the emission spectrum selector 430 or the angle of incidence between the filters and the excitation or emission light can be selected to the desired raw images at the lower and higher edges of the desired spectral edges. For example, in one embodiment, the detection moieties can have differences in spectra at their peaks of less than or equal to 50 nm. In one embodiment the detection moieties can have differences in spectra at their peaks of less than or equal to 10 nm. In one embodiment, the detection moieties can have differences in spectra at their peaks of 1-50 nm. In one embodiment, the detection moieties can have differences in spectra at their peaks of 1, 2, 3, 4, 5, 6, 7, 8, 9, 10, 11, 12, 15, 20, 25, 30, 40, 50, 60, 70, 75, 80, 90, or 100 nm. In one embodiment, the difference between successive spectra (such as at the peak) can be the same (e.g., first and second detection moieties are separated by 10 nm and second and third detection moieties are separated by 10 nm). In one embodiment, the differences between successive spectra (such as at the peak) can be different (e.g., first and second detection moieties are separated by 10 nm and second and third detection moieties are separated by 25 nm).

In one embodiment, the angle of incidence of light upon any filter can be 0.0°, 1.0°, 2.0°, 3.0°, 4.0°, 5.0°, 6.0°, 7.0°, 8.0°, 9.0°, 10.0°, 11.0°, 12.0°, 15.0°, 20.0°, 25.0°, 30.0°, 40.0°, 45.0°, 50.0°, 60.0°, 70.0°, 75.0°, 80.0°, 85.0°, or 89.9°. In one embodiment, the angle of incidence of light upon any filter can be up to, but not inclusive of, 90°. In one embodiment, the angle of incidence of light upon any filter can be less than 90°. In one embodiment, the angle of incidence of light upon any filter can be from 0.0° to 89.9°. As noted above, when there are two or more filters, each filter rotates freely and independently of the other filters, such that two or more filters can have the same angle of incidence or no two filters have the same angle of incidence. The angles of incidence are selected based on the desired wavelength to be obtained.

Any of the images or files, whether raw or processed, can be stored in any appropriate storage medium at any point during the performance of any embodiment of the present invention. The storage medium includes, but is not limited to, one or more of a hard disk, a random-access memory (RAM), a read only memory (ROM), a storage of distributed computing systems, an optical disk (such as a compact disc, digital versatile disc, or Blu-ray Disc), a flash memory device, a memory card, or the like.

Embodiments of the invention include a non-transitory computer readable medium which can store instructions for performing the above-described methods and any steps thereof, including any combinations of the same. For example, the non-transitory computer readable medium can store instructions for execution by one or more processors or similar devices.

Further embodiments of the present invention can also include a computer or apparatus (e.g. a phone, a tablet, a PDA, or the like) which reads out and executes computer executable instructions, such as a non-transitory computer-readable medium, recorded or stored on a storage medium (which may be the same as or different than the storage medium for storing images or files, as discussed above), to perform the functions of any embodiment. The computer may include one or more of a central processing unit (CPU), micro processing unit (MPU), or other circuitry, and may include a network of separate computers or separate computer processors. The computer executable instructions may be provided to the computer, for example, from a network or the storage medium.

The computer or apparatus can also be configured to display, such as on a monitor or screen, any of the images or files, whether raw or processed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially, graphically, or numerically relative terms, such as "under", "below", "lower", "over", "upper", "higher", and the like, may be used herein for ease of description to describe one element or feature's relationship to another element(s) or feature(s) as illustrated in the figures. It will be understood that the spatially relative terms are intended to encompass different orientations when in use or operation in addition to the orientation depicted in the figures. For example, if a device, system, or method, as depicted in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise. Additionally, "lower", "higher", and the like are used to depict elements, features, information, or the like which, relative to each other or at least other elements, features, information, or the like are further down or further up a chart, graph, or plot, or are lesser or greater in value or intensity.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention. Additionally, though "first" and "second" are used, the terms are not intended to limit various features/elements to only one or two. Rather, three (i.e., third), four (i.e., fourth), or more may be included or used where appropriate or desirous to do so.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

What is claimed is:

1. A method of analyzing a sample, the sample comprising a first detection moiety having a first emission spectrum, the first emission spectrum having a peak emission intensity at a peak intensity wavelength, a leading spectral edge with emission intensities less than the peak intensity at wavelengths less than the peak intensity wavelength, and a trailing spectral edge with emission intensities less than the peak intensity at wavelengths greater than the peak intensity wavelength, the method comprising:

acquiring, with an imaging device while stimulating the sample with excitation light, a first raw image of the sample at a first emission wavelength of the first emission spectrum, wherein the first emission wavelength is in the leading spectral edge or in the trailing spectral edge of the first emission spectrum, and wherein the first raw image comprises a first total signal comprising a first detection moiety signal at the first emission wavelength and a non-first detection moiety signal at the first emission wavelength;

acquiring, with the imaging device while stimulating the sample with excitation light, a second raw image of the sample at a second emission wavelength of the first emission spectrum, wherein the second emission wavelength is in the leading spectral edge or in the trailing spectral edge of the first emission spectrum, and wherein the second raw image comprises a second total signal comprising a first detection moiety signal at the second emission wavelength and a non-first detection moiety signal at the second emission wavelength; and outputting, with a processor, a final image of the first detection moiety based on the first and second raw images, wherein the first emission spectrum has a higher emission intensity for the first emission wavelength than for the second emission wavelength, and wherein the first and second emission wavelengths are in the same spectral leading edge or in the same spectral trailing edge of the first emission spectrum.

2. The method of claim 1, wherein the non-first detection moiety signal of the first raw image and the non-first detection moiety signal of the second raw image are caused by autofluorescence or background.

3. The method of claim 1, wherein the sample further comprises a second detection moiety having a second emission spectrum, wherein the non-first detection moiety signal of the first raw image and the non-first detection moiety signal of the second raw image are caused by the second detection moiety, the second emission spectrum having a peak emission intensity at a peak intensity wavelength, a leading spectral edge with emission intensities less than the peak intensity at wavelengths less than the peak intensity wavelength, and a trailing spectral edge with emission intensities less than the peak intensity at wavelengths greater than the peak intensity wavelength.

4. The method of claim 3, wherein the first emission wavelength at which the first raw image is acquired is in the leading spectral edge or the trailing spectral edge of the second emission spectrum, wherein the second emission wavelength at which the second raw image is acquired is in the same leading spectral edge or the same trailing edge of the second emission spectrum as the first emission wavelength, and wherein the second emission spectrum has a lower emission intensity for the first emission wavelength than for the second emission wavelength.

5. The method of claim 4, wherein the first emission wavelength in the leading spectral edge of the first emission spectrum and in the trailing spectral edge of the second emission spectrum.

6. The method of claim 5, wherein the second emission wavelength is in the leading spectral edge of the first emission spectrum and in the trailing spectral edge of the second emission spectrum.

7. The method of claim 4, wherein the leading edge of the first emission spectrum and the leading edge of the second emission spectrum have an offset of 1-50 nm, wherein the offset is the difference between wavelengths of the leading edge of the first emission spectrum and the leading edge of the second emission spectrum having the same emission intensity.

8. The method of claim 4, wherein the first emission wavelength is in the trailing spectral edge of the first emission spectrum and in the leading spectral edge of the second emission spectrum.

9. The method of claim 8, wherein the second emission wavelength is in the trailing spectral edge of the first emission spectrum and in the leading spectral edge of the second emission spectrum.

10. The method of claim 4, further comprising outputting, with the processor, a final image of the second detection moiety based on the first and second images.

11. The method of claim 10, further comprising displaying, on a screen, at least one of the final images of the first and second detection moieties to an end user or operator.

12. The method of claim 4, further comprising acquiring, with the imaging device while stimulating the sample with excitation light, a third raw image of the sample at a third emission wavelength of the second emission spectrum, wherein the third emission wavelength is in the same leading spectral edge or in the trailing spectral edge of the second emission spectrum as the first and second emission wavelengths, and wherein the third raw image comprises a third total signal comprising a second detection moiety signal at the third emission wavelength, and wherein the second emission spectrum has a higher emission intensity for the third emission wavelength than for the first and second emission wavelengths.

13. The method of claim 12, further comprising outputting, with the processor, a final image of the second detection moiety based on the second and third raw images.

14. The method of claim 12, further comprising:
tilting a first emission filter from a first angle of incidence to a second angle of incidence, wherein the tilting step of the first emission filter is performed between the acquisitions of the first and second raw images.

15. The method of claim 14, further comprising:
tilting the first emission filter from a third angle of incidence to a fourth angle of incidence, wherein the tilting step of the first emission filter is performed between the acquisitions of the second and third raw images.

16. The method of claim 15, wherein at least two of the first, second, third, and fourth angles are the same.

17. The method of claim 15, wherein none of the first, second, third, and fourth angles are the same.

18. The method of claim 14, further comprising:
tilting a second emission filter from a third angle of incidence to a fourth angle of incidence, wherein the tilting step of the second emission filter is performed between the acquisitions of the second and third raw images.

19. The method of claim 18, wherein at least two of the first, second, third, and fourth angles are the same.

20. The method of claim 18, wherein none of the first, second, third, and fourth angles are the same.

21. The method of claim 4, further comprising displaying, on a screen, at least one of the first and second raw images to an end user or operator.

22. The method of claim 1, wherein the first and second total signals are from pixels in the first and second raw images, respectively, corresponding to an identical location of the sample.

23. The method of claim 1, wherein a change between the first detection moiety signal of the first raw image and the first detection moiety signal of the second raw image is determined by one or more of the following operations or analyses: (1) change in signal intensity, (2) rate of signal change, (3) mathematical difference of signals between the respective raw images, (4) a first derivative of the signals of the respective raw images, or (5) signal thresholding.

24. The method of claim 1, further comprising:
tilting a first emission filter from a first angle of incidence to a second angle of incidence, wherein the tilting step of the first emission filter is performed between the acquisitions of the first and second raw images.

25. The method of claim 1, further comprising displaying, on a screen, at least one of the first and second raw images to an end user or operator.

26. The method of claim 1, further comprising displaying, on a screen, the final image of the first detection moiety to an end user or operator.

* * * * *